United States Patent
Narasimhan et al.

(10) Patent No.: US 7,566,348 B2
(45) Date of Patent: Jul. 28, 2009

(54) METHOD FOR COLORING HAIR

(75) Inventors: Saroja Narasimhan, Matawan, NJ (US); Lou Ann Christine Vena, Scotch Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 198 days.

(21) Appl. No.: 11/341,244

(22) Filed: Jan. 26, 2006

(65) Prior Publication Data

US 2007/0169286 A1    Jul. 26, 2007

(51) Int. Cl.
*A61Q 5/10*    (2006.01)
*A61Q 5/08*    (2006.01)

(52) U.S. Cl. .................. 8/405; 8/401; 8/406; 424/70.6; 132/202; 132/208

(58) Field of Classification Search .................. 8/401, 8/405, 406; 424/70.6; 132/202, 208
See application file for complete search history.

(56) References Cited

U.S. PATENT DOCUMENTS

| 4,566,875 A | * | 1/1986 | Grollier et al. | 8/406 |
| 2004/0016064 A1 | * | 1/2004 | Vena et al. | 8/406 |

* cited by examiner

*Primary Examiner*—Eisa B Elhilo
(74) *Attorney, Agent, or Firm*—Joy S. Goudie

(57) ABSTRACT

A two step high lift method for oxidatively coloring hair comprising a first step of applying to the hair a lifting mixture comprised of an aqueous oxidizing agent composition and a lifting composition to the hair for a period of time sufficient to lift the hair, followed by a second step of applying an inactivated oxidative dye composition for a period of time sufficient to color the hair, and a method for improving color vibrancy and tone, evenness of color, and reducing brassiness in high lift oxidatively colored hair.

2 Claims, No Drawings

METHOD FOR COLORING HAIR

TECHNICAL FIELD

The invention is in the field of oxidatively coloring hair, specifically, an improved method that permits oxidatively coloring dark hair to a lighter color without the associated drawbacks.

BACKGROUND OF THE INVENTION

It is always difficult and challenging to oxidatively color hair to a lighter color than the base hair shade, particularly when the base hair shade is black or very dark brown. There are basically two functions taking place in an oxidative hair color process: lifting and color deposit. Lifting involves bleaching melanin from the hair. Color deposit occurs when the oxidative dyes then impart color to the bleached hair strands. In order to oxidatively color hair to at least two shades lighter than the base hair shade it is critical that both lift and color deposit be optimal.

There are oxidative hair color kits on the market that purport to provide high lift and color deposit in one step. For example, L'Oréal Superior Preference® les True Brunettes is an oxidative hair color kit that the manufacturer states is for use in coloring dark hair to an ultra-lightening brown with no brassiness; and L'Oréal Féria Hi-Lift Browns a kit that the manufacturer advertises is suitable for lightening the color of very dark hair to a lighter brown shade. However, both kits provide for a one step process, e.g. the oxidative hair color is combined with a 30 volume developer and used to color the hair. The lifting and color deposit occurs in one step. While the process is generally effective, when lifting and coloring occur in one step the degree of lift (or lightening) is often not optimal. In addition, such processes generally provide color deposit that tends to be very ashy with purple or green tones. This occurs because the manufacturers of such colorants incorporate these shades to counteract the brassiness that sometimes occurs.

Further, even with kits like this it is difficult to obtain a final hair color that is more than two levels over the base hair color shade. Such products are also generally not acceptable for use on gray hair since they provide a tone that tends to be green or purple.

Salons have procedures for oxidatively coloring hair to a lighter shade that are completed in two steps. In the first step the hair is oxidatively colored with a high lift composition to remove melanin, followed by a second oxidative color procedure where an oxidative dye and developer are combined and the mixture is used to color the hair. However, this two step procedure involves application of oxidative compositions in both steps, which in turn may produce color that is less than optimal.

Accordingly, there is a need to provide an oxidative hair color method and compositions for lightening dark hair that will provide lightening that is up to, or greater than 2 levels more than the base hair color shade, but without brassiness and the other drawbacks associated with the traditional one step processes.

It is an object of the invention to provide a method for oxidatively coloring hair to a shade more than one or two levels lighter than the base hair color shade.

It is a further object of the invention to provide a method for oxidatively coloring dark hair to a lighter hair color.

It is a further object of the invention to provide a two step high lift method for oxidatively coloring hair to achieve hair color with improved vibrancy and reduced brassiness.

It is a further object of the invention to provide a two step high lift hair coloring method where the color deposit is true and vibrant.

SUMMARY OF THE INVENTION

The invention is directed to a two step high lift method for oxidatively coloring hair comprising a first step of applying to the hair a color lifting mixture for a period of time sufficient to lift the hair, followed by a second step of applying an inactivated oxidative dye composition for a period of time sufficient to color the hair.

The term "lift" means lightening. The term "high lift" when used herein means that the method of the invention is capable of lightening hair at least one to two levels above the base hair shade, preferably at least two levels.

The invention is further directed to a method for improving color vibrancy and reducing brassiness of oxidatively colored hair comprising treating the hair with a two step high lift method comprising a first step of applying to the hair a hair lifting mixture for a period of time sufficient to lift the hair, followed by a second step of applying an inactivated oxidative dye composition for a period of time sufficient to color the hair.

DETAILED DESCRIPTION

The method of the invention comprises the use of certain compositions according to certain procedures.

I. The Compositions Used in the Method

A. The Lifting Mixture

In order to achieve the lifting required in the first step of the invention process, the hair is treating with a lifting mixture. The lifting mixture is prepared immediately prior to use by combining an aqueous oxidizing agent composition and a hair lifting composition. When the two are combined the aqueous oxidizing agent composition activates the lifting composition such that the mixture is then operable to "lift" or bleach melanin from the hair fibers.

1. Aqueous Oxidizing Agent (or Developer) Composition

The developer or aqueous oxidizing agent composition in its simplest form is an aqueous solution of hydrogen peroxide. Preferably it comprises from about 1-99%, preferably 10-99%, more preferably 60-97% of water, and about 5-25%, preferably 6-20%, more preferably 7-15% by weight of the total composition of hydrogen peroxide. Developer compositions are generally sold in the form of 10, 20, 25, 30, or 40 volume hydrogen peroxide. The 20 volume hydrogen peroxide developer composition comprises 6% by weight of hydrogen peroxide. The 25 volume hydrogen peroxide developer composition contains about 7.5% of hydrogen peroxide and the 30 volume hydrogen peroxide developer composition about 9%, and the 40 volume developer about 12% hydrogen peroxide, with all weight percentages by weight of the total composition of hydrogen peroxide.

In the preferred embodiment of the invention, the developer composition used has a higher relative percentage of hydrogen peroxide, specifically about 25 to 30 volume or higher. Preferably, the aqueous oxidizing agent composition comprises from about 25 to about 50, preferably from about 25 to 40 volume hydrogen peroxide.

If desired, the developer composition may contain a variety of other ingredients that enhance the aesthetic properties and contribute to more efficient coloring of hair. Preferred developer compositions for use with the inactivated oxidative dye composition in the method of the invention, when combined with the oxidative dye composition, form a composition very similar in consistency to a shampoo. Suggested developer compositions preferably comprise:
 0.5-25% hydrogen peroxide,
 0.1-10% of a conditioner,
 0.01-5% of a thickener, and
 1-99% water.

(a). Conditioners

The developer composition may contain one or more conditioners that exert a conditioning effect on hair. If present such conditioners may range from about 0.1-30%, preferably from about 0.5-25%, more preferably from about 1-20% by weight of the total composition of one or more conditioners. Examples of suitable conditioning ingredients include, but are not limited to those set forth below.

(i). Cationic Silicones

As used herein, the term "cationic silicone" means any silicone polymer or oligomer having a silicon backbone, including polysiloxanes, having a positive charge on the silicone structure itself. Cationic silicones that may be used in the developer compositions of the invention include those corresponding to the following formula, where the ratio of D to T units, if present, are greater than about 80 D units to 1 T unit:

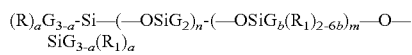

$(R)_a G_{3-a}-Si-(-OSiG_2)_n-(-OSiG_b(R_1)_{2-6b})_m-O-SiG_{3-a}(R_1)_a$ in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; R is a $C_{1-10}$ alkyl, and $R_1$ is a monovalent radical of the formula $C_qH_{2q}L$ in which q is an integer from 2 to 8 and L is selected from the groups:

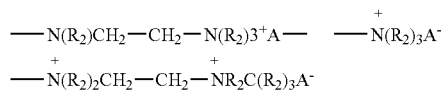

$-N(R_2)CH_2-CH_2-N(R_2)_3^+A^- \quad -N(R_2)_3^+A^-$
$-N(R_2)_2^+CH_2-CH_2-NR_2C(R_2)_3^+A^-$ in which $R_2$ is selected from the group consisting of H, phenyl, benzyl, a saturated hydrocarbon radical, and is preferably an alkyl radical containing 1-20 carbon atoms; and A- is a halide, methylsulfate, or tosylate ion.

Preferably the developer comprises one or more conditioners that exert a conditioning effect on hair. A variety of conditioners are suitable including cationic polymers, oily conditioning agents, fatty alcohols, proteins, and so on. A combined total weight of conditioners ranges from about 0.1-25%, preferably 0.5-20%, more preferably 1-15% by weight of the total composition.

(ii). Cationic Polymers

A variety of cationic polymers are suitable for use in the developer composition such as quaternary derivatives of cellulose ethers or guar derivatives, copolymers of vinylpyrrolidone, polymers of dimethyldiallyl ammonium chloride, acrylic or methacrylic polymers, quaternary ammonium polymers, and the like.

(aa). Quaternary Derivatives of Cellulose

Examples of quaternary derivatives of cellulose ethers are polymers sold under the tradename JR-125, JR-400, JR-30M. Suitable guar derivatives include guar hydroxypropyl trimonium chloride.

(bb). Copolymers of Vinylpyrrolidone

Copolymers of vinylpyrrolidone having monomer units of the formula:

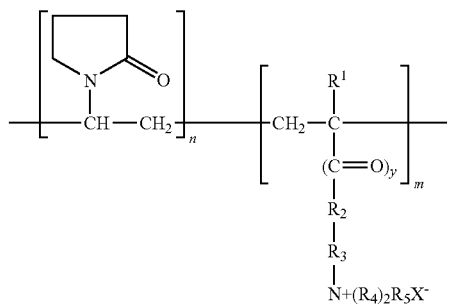

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or $-CH_2-CHOH-CH_2$, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

(cc). Polymers of Dimethyldiallylammonium Chloride

Homopolymers of dimethyldiallylammonium chloride or copolymers of dimethyldiallylammonium chloride and acrylamide are also suitable. Such compounds are sold under the tradename MERQUAT by Calgon.

(dd). Acrylic or Methacrylic Acid Polymers

Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters are suitable for use.

(ee). Polymeric Quaternary Ammonium Salts

Also suitable are polymeric quaternary ammonium salts of cellulose and other polymers, including but not limited to Polyquaternium 10, 28 31, 33, 34, 35, 36, 37, and 39.

(ff). Diquaternary Polydimethylsiloxanes

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

Particularly preferred are conditioners Polyquaternium 10 and Polyquaternium 28. Polyquaternium-10 is the polymeric quaternary ammonium salt of hydroxyethyl cellulose reacted with trimethyl ammonium substituted epoxide. Polyquaternium-28 is the polymeric quaternary ammonium salt consisting of vinyl pyrrolidone and dimethylaminopropyl methacrylamide monomers.

(gg). Oily Conditioning Agents

Also suitable are a variety of oily materials that provide good conditioning effect to hair. Suitable oils are liquid at room temperature and may comprise esters, hydrocarbons, and the like. Preferably the composition comprises 0.001-20%, more preferably 0.005-15%, most preferably 0.01-10% by weight of the total composition of such oils. Particularly preferred oily conditioning agents are oils extracted from vegetable sources, specifically meadowfoam seed oil.

(hh). Nonionic Silicones

Also suitable as conditioning agents are one or more silicones. Suitable silicone hair conditioning agents include volatile or nonvolatile nonionic silicone fluids, silicone resins, and silicone semi-solids or solids.

Volatile silicones are linear or cyclic silicones having a measurable vapor pressure, which is defined as a vapor pressure of at least 2 mm. of mercury at 20° C. Examples of volatile silicones are cyclic silicones having the general formula:

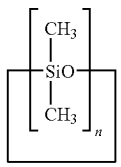

where n=3-7.

Also, linear volatile silicones that may be used in the compositions of the invention have the general formula:

where n=0-7, preferably 0-5.

Also suitable are nonvolatile silicone fluids including polyalkyl siloxanes, polyaryl siloxanes, polyalkylaryl siloxanes, polyether siloxane copolymers, amine-functional silicones, and mixtures thereof. Such silicones have the following general formula:

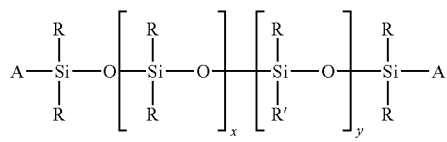

wherein R and R' are each independently alkyl, aryl, or an alkyl substituted with one or more amino groups, and x and y are each independently 0-100,000, with the proviso that x+y equals at least one and A is siloxy endcap unit. Preferred is where A is methyl, R is methyl, and R' is an alkyl substituted with at least two amino groups, most preferably an amine-functional silicone having the formula:

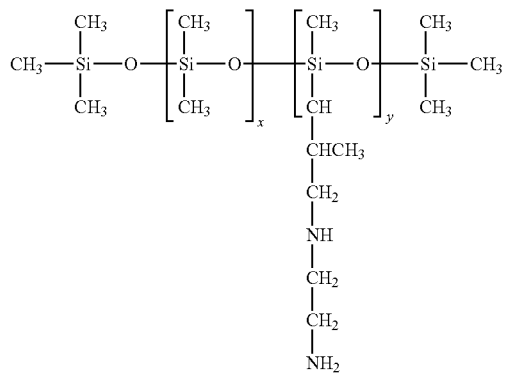

which is known by the CTFA name trimethylsilylamodimethicone.

Another type of silicone conditioning agent is a silicone polymer having the following general formula:

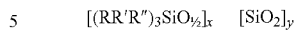

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3 SiO_{1/2}$ units to $SiO_2$ units is 0.75 to 1. Most preferred is this trimethylsiloxy silicate containing 2.4 to 2.9 weight percent hydroxyl groups, which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename Dow Corning 749 Fluid, which is a blend of about 40-60% volatile silicone and 40-60% trimethylsiloxy silicate (trimethylated silica). The fluid has a viscosity of 200-700 centipoise at 25° C., a specific gravity of 1.00 to 1.10 at 25° C., and a refractive index of 1.40-1.41.

(b). Thickeners

The developer composition may contain one or more thickeners that assist in maintaining an increased viscosity of the final composition resulting from mixture of the hair dye and the developer compositions. The amount of thickening agent if present is about 0.001-5%, preferably about 0.005-4%, more preferably about 0.005-3% by weight of the total composition.

A variety of thickening agents are suitable including those mentioned above with respect to the oxidative dye composition, in addition to low melting point waxes, carboxyvinyl polymers, and the like. Also suitable are a variety of water soluble anionic thickening polymers such as those disclosed in U.S. Pat. No. 4,240,450, which is hereby incorporated by reference. Suggested ranges of such polymers are about 0.01-5%, preferably 0.05-4%, more preferably 0.1-3% by weight of the total developer composition. Examples of such anionic polymers are copolymers of vinyl acetate and crotonic acid, graft copolymers of vinyl esters or acrylic or methacrylic acid esters, cross-linked graft copolymers resulting from the polymerization of at least one monomer of the ionic type, at least one monomer of the nonionic type, polyethylene glycol, and a crosslinking agent, and the like. Preferred are acrylate copolymers such as steareth-10 allyl ether acrylate copolymer.

(c). Other Ingredients (i). Nonionic Surfactants

The developer composition may contain one or more nonionic surfactants. Suitable nonionic surfactants are the same as those mentioned below with respect to the alkalizing composition, and in the same amount.

(ii). Chelating Agents

The developer composition may contain one or more chelating agents as described herein with respect to the oxidative dye composition, and in the same ranges by weight.

The aqueous oxidizing agent composition may contain one or more additional ingredients including but not limited to humectants, preservatives, botanicals, fatty acids, fatty alcohols, or mixtures thereof

2. The Lifting Composition

The lifting composition may comprise a persulfate bleach composition in particulate or semi-solid form, an alkalizing composition, or the combination of both. The term "alkalizing composition" means a composition that is typically used in high lift blonding processes. Such compositions typically contain no oxidative dyes or minimal oxidative dyes. If oxidative dyes are present they are those that are used in level 9, light blonde, or level 10, high lift blond oxidative hair color shades.

(a). Alkalizing Composition

The alkalizing composition comprises from about 0.1-99%, preferably from about 0.5-95%, more preferably from about 1-90% water, and from about 0.1-99%, preferably from about 0.5-95%, more preferably from about 1-90% by weight of the total composition of one or more oils. Suitable oils include those set forth above in the developer composition as conditioners or oily conditioning agents. The alkalizing composition may also contain other ingredients such as pH adjusters, botanicals, humectants, nonionic surfactants, fatty alcohols, fatty acids, and the like. In the event where the alkalizing composition contains oxidative dyes, they are dyes that are typically used in Level 9 or 10 oxidative hair color, including those noted in the tables set forth herein.

(i). Alkalizing Agent

The alkalizing composition preferably contains one or more alkalizing agents preferably in a range of about 1-5% based on the total weight of the alkalizing composition. The term "alkalizing agent" means an ingredient that is capable of imparting alkalinity (e.g. a pH of greater than 7) to the alkalizing agent composition. Suitable alkalizing agents include ammonium hydroxide, metal hydroxides, alkanolamines, sodium silicate, metal carbonates, sodium metasilicate, and mixtures thereof. Suitable metal hydroxides and carbonates include alkali metal and alkaline earth metal hydroxides or carbonates. Examples of such metal hydroxides include sodium, potassium, lithium, calcium, magnesium and so on. A particularly preferred alkaline earth metal hydroxide is sodium hydroxide. Suitable alkanolamines include mono-, di-, and trialkanolamines such as monoethanolamine (MEA), diethanolamine (DEA), triethanolamine (TEA), 2-aminobutanol, aminoethyl propanediol, aminomethyl propanediol, bis-hydroxyethyl tromethamine, diethanolamine, diethyl ethanolamine, diisopropanolamine, dimethylamino methylpropanol, dimethyl MEA, isopropanolamine, methylethanolamine, mixed isopropanolamines, triisopropanolamine, tromethamine, and mixtures thereof. A particularly preferred alkanolamine is MEA.

Most preferred are alkalizing agents that contain ammonium hydroxide in combination with a second alkalizing agent such as an alkanolamine.

(ii). Fatty Acids or Fatty Alcohols

The alkalizing composition may contain one or more fatty acids or fatty alcohols and if so suggested ranges are about 0.001-15%, preferably 0.005-10%, most preferably 0.01-8% by weight of the total composition. If fatty acids are present they may react with the alkalizing agent to form soap in situ, which provides a more shampoo-like character to the alkalizing composition when it is combined with the developer and applied to hair. Fatty acids are of the general formula RCOOH wherein R is a straight or branched chain, saturated or unsaturated $C_{6-30}$ alkyl. Suitable fatty alcohols are those of the general formula R—OH where R is as set forth for the fatty acid.

Examples of suitable fatty acids include oleic acid, stearic acid, myristic acid, linoleic acid, and so on. Particularly preferred is oleic acid.

Suitable fatty alcohols include stearyl alcohol, cetearyl alcohol, cetyl alcohol, or mixtures thereof.

(iii). Conditioners

Various hair conditioning agents, such as those mentioned for use in the developer composition, are also suitable for use in the alkalizing composition. If present such conditioners are suitable in the same percentage ranges as set forth for the developer.

(iv). Surfactants

(aa). Nonionic Surfactants

Nonionic surfactants may be present in the alkalizing composition. If so, suggested ranges are from about 0.01-10%, preferably about 0.05-8%, more preferably about 0.1-7% by weight of the total composition. Suitable nonionic surfactants include alkoxylated alcohols or ethers, alkoxylated carboxylic acids, sorbitan derivatives, and the like.

(1). Alkoxylated Alcohols or Ethers

Suitable alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2-30, which is formed by the reaction of stearyl alcohol and ethylene oxide where the number of repeating ethylene oxide units is 2 to 30; Oleth 2-30 which is formed by the reaction of oleyl alcohol and ethylene oxide where the number of repeating ethylene oxide units is 2 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. Particularly preferred are Steareth-21, which is the reaction product of a mixture of stearyl alcohol with ethylene oxide, and the number of repeating ethylene oxide units in the molecule is 21, and Oleth-20 which is the reaction product of oleyl alcohol and ethylene oxide wherein the number of repeating ethylene oxide units in the molecule is 20.

(2). Alkoxylated Carboxylic Acids

Also suitable as the nonionic surfactant are alkyoxylated carboxylic acids, which are formed by the reaction of a carboxylic acid with an alkylene oxide or with a polymeric ether. The resulting products have the general formula:

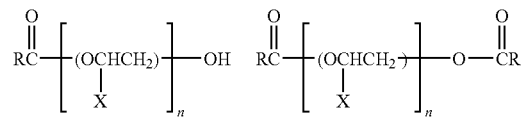

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1-100.

(3). Sorbitan Derivatives

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates.

Examples of such ingredients include Polysorbates 20-85, sorbitan oleate, sorbitan palmitate, sorbitan sesquiisostearate, sorbitan stearate, and so on.

(bb). Anionic Surfactants

If desired the alkalizing composition may contain one or more anionic surfactants. Together with the soap formed by the reaction of the fatty acid and alkanolamine or metal hydroxide, the ingredients provide the composition with the characteristics of shampoo. Preferred ranges of anionic surfactant, if present, are from about 0.1-25%, preferably 0.5-20%, more preferably 1-15% by weight of the total composition.

(1). Alkyl and Alkyl Ether Sulfates

Suitable anionic surfactants include alkyl sulfates or alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

(2). Sulfate Derivatives

Another type of anionic surfactant which may be used in the compositions of the invention are water soluble salts of organic, sulfuric acid reaction products of the general formula:

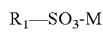

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

(3). Isethionic Acid Derivatives

Also suitable as anionic surfactants are reaction products of fatty acids esterified with isethionic acid and neutralized with sodium hydroxide. The fatty acids may be derived from coconut oil, for example.

(4). Succinates or Succinimates

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

(5). Olefin Sulfonates

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

(6). Beta-Alkoxy Alkane Sulfonates

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

(7). N-Acyl Amino Acids

Still another class of anionic surfactants include N-acyl amino acid surfactants and salts thereof (alkali, alkaline earth, and ammonium salts) having the formula:

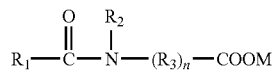

wherein $R_1$ is a $C_{8-24}$ alkyl or alkenyl radical, preferably $C_{10-18}$; $R_2$ is H, $C_{1-4}$ alkyl, phenyl, or $-CH_2COOM$; $R_3$ is $CX_2-$ or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

(cc). Amphoteric or Zwitterionic Surfactants

Also suitable for use in the alkalizing composition are amphoteric or zwitterionic surfactants. Examples of amphoteric surfactants that can be used are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

(v). Botanicals

It may be desired to include one or more botanicals in the alkalizing composition. Suitable botanicals include various extracts such as hypnea musciformis, gellidiela acerosa, sargassum filipendula, and so on.

2. Persulfate Bleach Composition

Also suitable as the lifting composition is a persulfate bleach composition. The bleach composition may be in the form of a powder, paste, cream, or liquid. The persulfate composition generally comprises a mixture of persulfate compounds which are capable of bleaching the hair, particulate fillers, and, if desired, inorganic particulate colorants. The persulfate composition may be found in the powdered particulate form, or in the form of a cream or paste as described in U.S. Pat. No. 5,888,484; and U.S. Pat. No. 6,613,311, both of which are hereby incorporated by reference in their entirety.

(a). Persulfates

The persulfate composition comprises about 15-65%, preferably about 20-60%, more preferably about 25-55% by weight of the total persulfate composition of one or more inorganic persulfates which may be alkali metal or alkaline earth metal persulfates, or ammonium persulfate.

(b). Alkalizing Agents

The persulfate composition preferably contains one or more alkalizing agents. Preferred alkalizing agents are one or more inorganic salts as set forth herein. Suggested ranges of inorganic salts are from about 0.1-40%, preferably about 0.5-35%, preferably about 1-30% by weight of the total composition.

(c). Particulate Fillers

The persulfate composition also preferably comprises one or more particulate fillers. Preferably, the persulfate composition comprises about 5-60%, preferably about 8-55%, more preferably about 10-50% by weight of the total persulfate composition of the particulate fillers. The term "particulate filler" means a generally inert particulate having a particle size of about 0.1-250 microns. The particulate fillers provide volume and, when mixed with the persulfates, dilute the persulfate particles. A variety of particulate fillers are suitable including inorganics, inorganic salts, hydrophilic colloids, carbohydrates, soaps, alkyl sulfates, and the like.

(i) Inorganics

Examples of inorganics include silica, hydrated silica, alumina, attapulgite, bentonite, calcium oxide, chalk, diamond powder, diatomaceous earth, fuller's earth, hectorite, kaolin, mica, magnesium oxide, magnesium peroxide, montmorillonite, pumice, talc, tin oxide, zeolite, zinc oxide, and the like.

(ii) Hydrophilic Colloids

Examples of suitable hydrophilic colloids include hydroxyethylcellulose, locust bean gum, maltodextrin, methylcellulose, agar, dextran, dextran sulfate, gelatin, pectin, potassium alginate, sodium carboxymethylchitin, xanthan gum, and the like.

(iii) Carbohydrates

Examples of suitable carbohydrates include sugars such as glucose, sucrose, maltose, xylose, trehelose, and derivatives thereof, in particular sugar esters of long chain, $C_{14-30}$ fatty acids, as well as dextrins, cellulosics, and derivatives thereof.

(iv) Soaps and Alkyl Sulfates

Examples of soaps and alkyl sulfate particles that may act as particulate fillers include the aluminum, sodium, and potassium salts of fatty acids such as aluminum distearate, aluminum isostearate, aluminum myristate, calcium behenate, calcium stearate, calcium behenate, magnesium stearate, magnesium tallowate, potassium palmitate, potassium stearate, potassium oleate, sodium stearate, sodium oleate, sodium myristate, sodium palmitate, and the like. Suitable alkyl sulfates include sodium lauryl sulfate, sodium cetyl sulfate, sodium myristyl sulfate, sodium octyl sulfate, and the like.

(d). Inorganic Colorants

If desired, the persulfate composition may comprise about 0.01-2%, preferably about 0.05-1%, more preferably about 0.1-1% by weight of the total persulfate composition of an inorganic colorant. The inorganic colorant is preferably in the particulate form and will provide a subtle coloration to the powder composition to make it more aesthetically pleasing for commercial purposes. Particularly preferred for use in the bleach composition is ultramarine blue.

B. The Inactivated Dye Composition

In the method of the invention, in the second step, an inactivated dye composition is applied to the hair. The term "inactivated" means that the dye composition has not been combined with an aqueous oxidizing agent composition in a pre-mix prior to application to the hair. Rather, according to the method of the invention, the hair is first treated with the lifting mixture obtained by combining the aqueous oxidizing agent and the lifting composition for the requisite period of time. Thereafter, the inactivated dye composition is applied on top of the lifting mixture already on the hair.

The inactivated dye composition may be in a liquid, solid, or semi-solid form. It may be in a shampoo, conditioner, or any other type of composition form. The inactivated dye composition generally contains at least one oxidative primary intermediate that is operable to color hair when in the oxidized or activated form, which occurs when the inactivated dye composition is applied to the hair on top of the developer composition. The composition generally comprises from about 0.01-35%, preferably from about 0.1-25%, more preferably from about 0.5-20% by weight of the total composition of at least one oxidative dye; and from about 0.01-95%, preferably about 0.05-95%, preferably about 0.1-85% by weight of the total composition of water. The composition may be in the form of a solution or emulsion. If the latter, the emulsion generally comprises from about 0.01-95%, preferably about 0.05-85%, more preferably about 0.1-80% by weight of the total composition of water and about 0.01-80%, preferably about 0.1-65%, preferably about 0.5-50% by weight of the total composition of an oily phase. The first composition may comprise a variety of other ingredients as further described herein.

1. Oxidative Dyes (a). Primary Intermediates.

The inactivated oxidative dye composition comprises at least one primary intermediate and, optionally, at least one coupler for the formation of oxidative dyes. It is noted that the primary intermediates and optional couplers that are found in the inactivated dye composition are generally selected to impart the desired color to the hair. This is in contrast to the optional oxidative dyes that may be found in the lightening mixture, which are selected to impart maximum bleaching or lifting of the hair.

Suitable ranges of primary intermediates are about 0.0001-6%, preferably about 0.0005-5.5%, more preferably about 0.001-5% by weight of the total composition. Such primary intermediates are well known for use in hair color, and include ortho or para substituted aminophenols or phenylenediamines, including para-phenylenediamines of the formula:

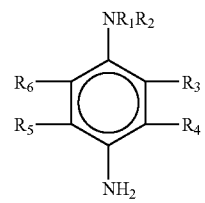

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Specific examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

(b). Color Coupler

The inactivated oxidative dye composition may optionally comprise from about 0.0001-10%, more preferably about 0.0005-8%, most preferably about 0.001-7% by weight of the total oxidative composition of one or more color couplers. Suitable color couplers include, for example, those having the general formula:

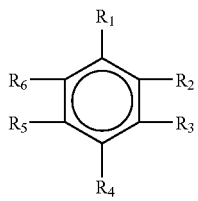

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methylpyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3 [(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Preferred couplers include resorcinol, 1-naphthol, 2-methylresorcinol, 4-amino-2-hydroxy toluene, m-aminophenol, 2,4-diaminophenoxyethanol, phenyl methylpyrazolone, their salts, or mixtures.

In the haircolor industry, haircolor is classified into one of ten levels as follows:

| |
|---|
| 1 = very black |
| 2 = bright black |
| 3 = very dark brown |
| 4 = dark brown |
| 5 = medium brown |
| 6 = light brown |
| 7 = dark blonde |
| 8 = medium blonde |
| 9 = light blonde |
| 10 = high lift blonde |

Set forth in the table below is a non-limiting example of the primary intermediates and the color couplers that may be used in various shades of hair color. Other primary intermediates and couplers may be used in addition to, or in lieu of, those set forth in the Table and nothing herein shall be construed to limit the invention to only those primary intermediates and couplers set forth.

| Level 1 - Very Black | | Level 2 - Bright Black | |
|---|---|---|---|
| Primary Intermediates | Couplers | Primary Intermediates | Couplers |
| p-phenylenediamine | m-aminophenol | p-phenylenediamine | resorcinol |
| p-phenylenediamine sulfate | resorcinol | 2-chloro-P-phenylenediamine sulfate | |
| 2-chloro-phenylene diamine sulfate | 4-amino-2-hydroxy toluene | o-aminophenol | |
| p-aminophenol | 4-chlororesorcinol | | |
| o-aminophenol | m-aminophenol HCL | | |
| | 2,4-diaminophenoxy ethanol | | |
| | m-phenylenediamine sulfate | | |

| Level 3 - Very Dark Brown | | Level 4 - Dark Brown | |
|---|---|---|---|
| Primary Intermediates | Couplers | Primary Intermediates | Couplers |
| p-phenylenediamine N,N-bis(2-hydroxyethyl)-P-phenylenediamine sulfate | resorcinol 1-naphthol | p-phenylenediamine N,N-bis(2-hydroxyethyl)-P-phenylene diamine sulfate | resorcinol 1-naphthol |
| | m-aminophenol | p-aminophenol | m-aminophenol |
| | | | phenyl methyl pyrazolone |
| | | o-aminophenol | 4-amino-2-hydroxytoluene |

| Level 5 - Medium Brown | | Level 6 - Light Brown | |
|---|---|---|---|
| Primary Intermediates | Couplers | Primary Intermediates | Couplers |
| p-phenylenediamine N,N-bis(2-hydroxyethyl)-P-phenylene | resorcinol 1-naphthol | p-phenylenediamine N,N-bis(2-hydroxyethyl)-P-phenylene | resorcinol 1-naphthol |

-continued

| Level 5 - Medium Brown | | Level 6 - Light Brown | |
|---|---|---|---|
| Primary Intermediates | Couplers | Primary Intermediates | Couplers |
| diamine sulfate | | diamine sulfate | |
| p-aminophenol | m-aminophenol | p-aminophenol | m-aminophenol |
| o-aminophenol | phenyl methyl pyrazolone | | phenyl methyl pyrazolone |
| | 2-methyl-resorcinol | | 4-amino-2-hydroxy toluene |
| | 4-amino-2-hydroxtoluene | | 2-methyl-resorcinol |

| Level 7 - Dark Blonde | | Level 8 - Medium Blonde | |
|---|---|---|---|
| Primary Intermediates | Couplers | Primary Intermediates | Couplers |
| p-phenylenediamine | resorcinol | p-phenylenediamine | resorcinol |
| N,N-bis(2-hydroxy-ethyl)-P-phenylene diamine sulfate | 1-naphthol | N,N-bis(2-hydroxyethyl)-P-phenylenediamine sulfate | 1-naphthol |
| p-aminophenol | phenyl methyl pyrazolone | p-aminophenol | m-aminophenol |
| o-aminophenol | | | phenyl methyl pyrazolone |
| | | | 4-amino-2-hydroxytoluene |

| Level 9 - Light Blonde | | Level 10 - High Lift Blonde | |
|---|---|---|---|
| Primary Intermediates | Couplers | Primary Intermediates | Couplers |
| p-phenylenediamine | resorcinol | p-phenylenediamine | resorcinol |
| N,N-bis(2-hydroxyethyl)-P-phenylenediamine sulfate | 4-amino-2-hydroxy toluene | N,N-bis(2-hydroxyethyl)-P-phenylenediamine sulfate | 1-naphthol |
| p-aminophenol | phenyl methyl pyrazolone | | phenyl methyl pyrazolone |
| o-aminophenol | 2-methyl-resorcinol 1-naphthol | | 2-methyl-resorcinol |

The inactivated oxidative dye composition may also contain a variety of other ingredients such as surfactants, conditioners, humectants, pigments, and the like.

2. Surfactants

The inactivated oxidative dye composition may comprise one or more surfactants that may assist in maintaining the composition in the emulsion form if it is an emulsion, or aid in the foaming or cleansing capability of the composition if it is in the shampoo form. Suitable surfactants include anionic surfactants, nonionic surfactants, amphoteric surfactants, and the like. If present, surfactants may range from about 0.001-50%, preferably about 0.005-45%, more preferably about 0.1-40% by weight of the first composition.

(a) Nonionic Surfactants

Suggested ranges of nonionic surfactant, if present, are about 0.01-10%, preferably about 0.05-8%, more preferably about 0.1-7% by weight of the total oxidative composition. Suitable nonionic surfactants include alkoxylated alcohols or ethers, alkoxylated carboxylic acids, sorbitan derivatives, and the like.

Suitable alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2-30, which is formed by the reaction of stearyl alcohol and ethylene oxide where the number of repeating ethylene oxide units is 2 to 30; Oleth 2-30 which is formed by the reaction of oleyl alcohol and ethylene oxide where the number of repeating ethylene oxide units is 2 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Also suitable as the nonionic surfactant are alkyoxylated carboxylic acids, which are formed by the reaction of a carboxylic acid with an alkylene oxide or with a polymeric ether. The resulting products have the general formula:

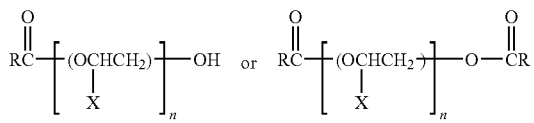

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1-100.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on.

(b) Anionic Surfactants

If desired the first composition may contain one or more anionic surfactants. Preferred ranges of anionic surfactant are about 0.01-25%, preferably 0.5-20%, more preferably 1-15% by weight of the total oxidative composition. Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

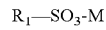

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide, or fatty acids reacts with alkanolamines or ammonium hydroxides. The fatty acids may be derived from coconut oil, for example. Examples of fatty acids also include lauric acid, stearic acid, oleic acid, palmitic acid, and so on.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones, which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

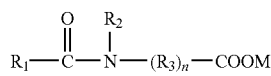

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_2$— or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

(c). Cationic, Zwitterionic or Betaine Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

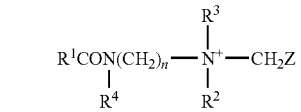

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula

or iminodialkanoates of the formula:

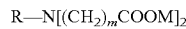

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention. The general formula for such surfactants is:

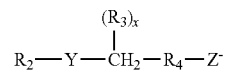

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionic surfactants include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like.

3. Polar Solvents

The inactivated oxidative dye composition may also comprise a variety of polar solvents other than water, including mono-, di-, or polyhydric alcohols, and similar water soluble ingredients. If present, such polar solvents may range from about 0.01-25%, preferably about 0.05-15%, more preferably about 0.1-10% by weight of the first composition of polar solvent. Examples of suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like. Many of these types of alcohols also serve also serve as penetration enhancers, meaning that they enhance penetration of primary intermediates and couplers into the hair shaft by virtue of their tendency to act as humectants and swell the hair shaft. Ethoxydiglycol is a particularly good penetration enhancer and is the preferred polar solvent.

In the preferred embodiment of the invention the composition comprises water in addition to one or more polar solvents, which are dihydric alcohols. In the preferred compositions, about 0.001-20%, preferably about 0.005-10%, more preferably about 0.001-8% by weight of the total composition comprises a non-aqueous polar solvent.

4. Chelating Agents

The inactivated oxidative dye composition may also contain 0.0001-5%, preferably 0.0005-3%, more preferably 0.001-2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

5. pH Adjusters

It may also be desirable to add small amounts of acids or bases to adjust the pH of the first composition to the desired pH range of greater than about 7.0 to 12.0. Suitable acids include hydrochloric acid, phosphoric acid, erythorbic acid, and the like. Suitable bases include sodium hydroxide, potassium hydroxide, and the like. Also suitable are primary, secondary, or tertiary amines or derivative thereof such as aminomethyl propanol, monoethanolamine, and the like. Suggested ranges of pH adjusters are from about 0.00001-8%, preferably about 0.00005-6%, more preferably about 0.0001-5% by weight of the total composition.

6. Preservatives

The inactivated oxidative dye composition may also contain one or more preservatives. Suggested ranges are about 0.0001-8%, preferably 0.0005-7%, more preferably about 0.001-5% by weight of the total composition. Suitable preservatives include methyl, ethyl, and propyl paraben, hydantoins, and the like.

In the preferred method of the invention the inactivated oxidative dye composition is in the form of a liquid such as a shampoo or conditioner composition.

II. The Method

A. The First Step

The method for coloring hair is in two steps. In the first step the hair is treated with the lifting mixture, which is prepared by combining the aqueous oxidizing agent and the lifting composition. In the case where the lifting composition in the lifting mixture comprises a persulfate bleach composition, from about 1 to 2 parts, preferably about 1.5 parts, aqueous oxidizing agent composition are combined with 0.5 to 2 parts, preferably about 1.0 parts persulfate bleach composition. In the case where the lifting mixture is an alkalizing composition, from about 1 to 2 parts aqueous oxidizing agent composition and about 0.5 to 2 parts alkalizing composition are combined to form the lifting mixture which is then applied to the hair. The proportions mentioned may vary depending on the type of hair, the hair length, and the desired properties.

The lifting mixture is applied to the hair strands ensuring that all hair strands are coated. The lifting mixture is left on the hair for a period of time necessary to achieve adequate lifting. In general, this period of time is from about 10-45 minutes, preferably from about 15-35 minutes, more preferably about 20 minutes. Thereafter, preferably, additional lifting mixture is added to the root area of the hair and the composition is left for an additional period of time ranging from about 5 to 15 minutes, preferably about 10 minutes.

Then, the inactivated oxidative dye composition is applied to the hair on top of the lifting mixture and massaged into the hair for a period of time ranging from about 1 to 15, preferably from about 1 to 8, most preferably about 2 minutes.

The mixture is rinsed well from the hair with water. If desired the hair may be treated with standard shampoo and conditioner.

Hair colored according to the two step method of the invention exhibits improved vibrancy and color tone. In addition, dark hair can be lightened more than one or two levels above the base hair shade. In general, the method of the invention permits oxidative coloring of the hair where the hair is lightened from one to five, preferably from two to four levels above the base hair color shade.

III. Kits

The compositions necessary to practice the method of the invention may be present in kit form, such as retail kits. Such kits generally contain a carton or box for holding the various kit components. The kit will contain one receptacle containing an aqueous oxidizing agent composition, a second receptacle containing the lifting composition, and a third receptacle containing the inactivated dye composition. If desired, the kit may contain other ingredients such as printed documents (like instructions, discount coupons, etc.), gloves, and so on.

The invention will be further described in connection with the following examples which are set forth for the purposes of illustration only.

EXAMPLE 1

A 30 volume developer for use in the method of the invention was prepared as follows:

| Ingredient | w/w % |
| --- | --- |
| Water | QS |
| Methyl paraben | 0.05 |
| EDTA | 0.02 |
| Mineral oil | 0.60 |
| Cetearyl alcohol/ceteareth-20 | 4.50 |

-continued

| Ingredient | w/w % |
|---|---|
| Lauramide MEA | 0.01 |
| Cetearyl alcohol | 0.20 |
| Cyclomethicone/trimethylsiloxysilicate (50:50) | 0.01 |
| Amodimethicone/C11-15 Pareth-7, Laureth-9, Trideceth-12, glycerin, water | 2.00 |
| Hydrogen peroxide (35% aqueous solution) | 26.00 |
| Steareth-10 allyl ether/acrylates copolymer | 0.10 |
| Disodium phosphate | 0.03 |
| Phosphoric acid | 0.028 |

The composition was prepared by combining the ingredients and mixing well. The composition was stored in a plastic container.

EXAMPLE 2

Alkalizing compositions were prepared as follows:

| | w/w % | |
|---|---|---|
| Ingredient | A | B |
| Water | QS | QS |
| Erythrobic acid | 0.20 | 0.20 |
| Sodium sulfite | 0.50 | 0.50 |
| Ethoxydiglycol | 5.00 | 5.00 |
| Tetrasodium EDTA | 0.80 | 0.80 |
| Ethanolamine | 3.00 | 3.00 |
| *Hypnea Musciformis* Extract, *Gelligiela Acerosa* Extract, *Sargassum Filipendula* Extract, Sorbitol | 0.80 | 0.80 |
| Sodium benzotriazolyl butylphenol sulfonate, buteth-3, tributyl citrate | 0.50 | 0.50 |
| P-phenylendiamine | 0.001 | — |
| 1-naphthol | 0.002 | — |
| P-aminophenol | — | 0.01 |
| Resorcinol | — | 0.01 |
| Ammonium lauryl sulfate | 2.00 | 2.00 |
| Oleic acid | 12.50 | 12.50 |
| Cetearyl alcohol | 4.00 | 4.00 |
| Cetearyl alcohol, polysorbate-60 | 2.00 | 2.00 |
| Oleth-20 | 1.00 | 1.00 |
| Steareth-21 | 0.70 | 0.70 |
| *Limananthes Alba* (meadowfoam) seed oil | 0.75 | 0.75 |
| Oleyl alcohol | 0.40 | 0.40 |
| Polyquaternium-10 | 0.20 | 0.20 |
| Polyquaternium-28 | 0.50 | 0.50 |
| Mica, titanium dioxide | 0.30 | 0.30 |
| Hydrolyzed wheat protein | 0.50 | 0.50 |
| Fragrance | 1.25 | 1.25 |
| Ammonium hydroxide (28%) | 13.00 | 13.00 |

The compositions were prepared by combining the ingredients and mixing well. The compositions were stored in brown glass containers.

EXAMPLE 3

A lifting composition in the form of a persulfate bleach was prepared as follows:

| | w/w % |
|---|---|
| Potassium persulfate | 45.00 |
| Sodium persulfate | 5.00 |
| Sodium metasilicate | 11.50 |
| Silica | 2.00 |
| Hydrated silica | 2.00 |

-continued

| | w/w % |
|---|---|
| Sodium stearate | 10.67 |
| EDTA | 2.00 |
| Hydroxyethylcellulose | 3.09 |
| Sodium lauryl sulfate | 2.00 |
| Sodium chloride | 5.00 |
| Sucrose | 7.16 |
| Ultramarine blue | 0.08 |
| Sodium silicate | 4.50 |

EXAMPLE 4

Split head tests were conducted on a salon panelist having dark brown hair having from about 10 to 70 gray hairs on her whole head. The developer composition of Example 1, 1.5 parts, and the alkalizing composition A from Example 2, 1 part, were combined to form a lifting mixture which was applied to strands of hair on the left side of the head, generally avoiding the root area for 20 minutes. Additional lifting mixture was then applied to the root area for an additional 10 minutes. An inactivated oxidative dye composition having the following formula was applied on the left side over the lifting mixture for 2 minutes.

| Ingredient | % by weight |
|---|---|
| Water | QS |
| Citric acid | 0.001 |
| Erythrobic acid | 0.50 |
| Sodium sulfite | 0.50 |
| Ethoxydiglycol | 2.00 |
| P-Phenylenediamine | 2.00 |
| M-aminophenol | 0.80 |
| Resorcinol | 1.10 |
| 4-amino-2-hdroxytoluene | 0.10 |
| Hydroxypropylmethylcellulose | 0.30 |
| Tetrasodium EDTA | 0.30 |
| Sodium lauryl sulfate (30% aqueous solution) | 10.00 |
| Sodium laureth sulfate (28% aqueous solution) | 20.00 |
| Cocamidopropyl betaine | 4.00 |
| Ethanolamine | 2.50 |
| Isostearic acid | 6.00 |
| Lauramide DEA | 2.00 |
| Fragrance | 0.75 |

After the color mixture was rinsed from the hair with lukewarm water until the water ran clear, a hair conditioner of the following formula was applied for two minutes, then rinsed out with water.

| Ingredient | w/w % |
|---|---|
| Water | QS |
| Methyl paraben | 0.20 |
| Propyl paraben | 0.05 |
| Panthenol | 0.01 |
| Behentrimonium chloride | 4.00 |
| Glycerin | 5.00 |
| Cetearyl alcohol | 6.00 |
| Mango seed butter | 0.10 |
| Amodimethicone, cetrimonium chloride, trideceth-12 | 3.30 |
| Sodium benzotriazolyl Butylphenol Sulfonate, Buteth-3, Tributyl Citrate | 0.005 |
| Fragrance | 0.50 |
| Cholesteryl oleyl carbonate, cholesteryl chloride, cholesteryl nonanoate | 0.01 |

-continued

| Ingredient | w/w % |
|---|---|
| Isostearyl lactate, diisostearyl malate, triisostearyl citrate, isostearyl glycolate | 0.01 |
| Citric acid | 0.015 |
| Methylchloroisothiazolinone, methylisothiazolinone | 0.04 |
| Polyethylene terephthalate, acrylates copolymer | 0.30 |

The right side of the head was treated with L'Oréal Féria Hi-Lift Browns™. The ingredient listing on this product is reproduced below:

Shimmering Colour Permanent Haircolour Gel Ingredients: Water, Trideceth-2 Carboxamide MEA, Propylene Glycol, Hexylene Glycol, PEG-2 Oleamine, Ammonium Hydroxide, Polyglyceryl-4-Oleyl Ether, Oleyl Alcohol, Alcohol Denat., Polyglyceryl-2-Oleyl Ether, Oleic Acid, Sodium Diethylaminopropylcocoaspartamide, Pentasodium Pentetate, Fragrance, Ammonium Acetate, Sodium Metabisulfite, Phenyl Methyl Pyrazolone, Resorcinol, Erythorbic Acid, P-Phenylenediamine, 2,4-Diaminophenoxyethanol HCL, m-Aminophenol, Hydroxypropyl Bis(N-Hydroxyethyl-p-Phenylenediamine)HCL.

Shimmering Colour Developing Crème Ingredients: Water, Hydrogen Peroxide, Cetearyl Alcohol, Trideceth-2 Carboxamide MEA, Ceteareth-30, Glycerin, Pentasodium Pentetate, Sodium Stannate, Tetrasodium Pyrophosphate.

Colour Hydrator No Build-Up Deep Conditioner Ingredients: Water, Cetearyl Alcohol, Glycerin, Behentrimonium Chloride, Euphorbia Cerifera (Candelilla) Wax, Amodimethicone, Cetyl Esters, Isopropyl Alcohol, Fragrance, Methylparaben, Trideceth-12, Chlorhexidine Dihydrochloride, Cetrimonium Chloride.

The other half head was treated according to package instructions. The bottle of Shimmering Colour Permanent Haircolour Gel was poured into the Shimmering Colour Developing Crème and mixed well. The majority of the composition was immediately applied to unwashed dry hair for 20 minutes, covering only the ends of the hair and avoiding the roots. The remaining portion of the composition was then applied to the hair roots for 10 minutes. After 30 minutes the mixture was rinsed from the hair with lukewarm water until the rinse water was clear. The Colour Hydrator No Build-Up Deep Conditioner was applied to hair for two minutes, then rinsed out with water.

A trained salon evaluator evaluated the results on both sides. The color tone, evenness of color, lift, and color vibrancy in the hair treated with the method of the invention was better than these same properties on the half head treated with the L'Oréal product.

EXAMPLE 5

A salon panelist having dark brown hair with about 10 to 70 gray hairs on the entire head was recruited for this study. A split head test was conducted. The left side of the head was treated with a lifting mixture obtained by combining about 1.5 parts of the developer composition of Example 1 and about 1 part of alkalizing composition A from Example 2. The developer composition was applied to the hair strands, avoiding the root area, and left for 20 minutes. Additional lifting mixture was then applied to the root area for 11 minutes. The inactivated oxidative dye composition as set forth in Example 2 was applied for 2 minutes. The mixture was rinsed from the hair with lukewarm water until the water ran clear. Hair conditioner as set forth in Example 4 was applied to the hair for 2 minutes, then rinsed out with water.

The other half head was treated with L'Oréal New Ultra-Lightening for Dark Hair Only Superior Preference® les True Brunettes, Level 3 permanent hair color UL53 (ultra light beige brown) following the package instructions. The ingredient listing for the products in the kit are set forth below:

Color Gel Ingredients: Water, Trideceth-2 Carboxamide MEA, Propylene Glycol, Hexylene Glycol, PEG-2 Oleamine, Ammonium Hydroxide, Polyglyeryl-4-Oleyl Ether, Oleyl Alcohol, Alcohol Denat., Polyglyceryl-2-Oleyl Ether, Oleic Acid, Sodium Diethylaminopropyl Cocoaspartamide, Pentasodium Pentetate, Ammonium Acetate, Fragrance, Sodium Metabisulfite, Resorcinol, P-Phenylenediamine, m-Aminophenol, Phenyl Methyl Pyrazolone, Erythorbic Acid, P-Aminophenol, 2-Methylresorcinol, Hydroxypropyl Bis(N-Hydroxyethyl-p-Phenylenediamine) HCL, 2,4-Diaminophenoxyethanol HCL, 2-Methyl-5-Hydroxyethyl-Aminophenol, p-Methylaminophenol sulfate.

Color Optimizing Crème Ingredients: Water, Hydrogen Peroxide, Cetearyl Alcohol, Trideceth-2 Carboxamide MEA, Ceteareth-30, Glycerin, Pentasodium Pentetate, Sodium Stannate, Tetrasodium Pyrophosphate.

Care Supreme® Conditioner Ingredients: Water, Cetearyl Alcohol, Glycerin, Behentrimonium Chloride, Euphorbia Cerifera (candelilla) wax, Amodimethicone, Cetyl Esters, Isopropyl Alcohol, Fragrance, Methylparaben, Camphor Benzalkonium Methosulfate, Trideceth-12, Chlorhexidine, Dihydrochloride, Cetrimonium Chloride, PPG-5-Ceteth-20, Oleth-10, Disodium Cocoamphodipropionate, Lecithin, Phosphoric Acid, Tocopherol, Ethyl Hexyl Salicylate, Phenoxyethanol, Ethyl Paraben.

A trained salon evaluator assessed the difference between the half heads. The color tone, evenness of color, lift, and color vibrancy in the hair treated with the method of the invention was better than these same properties on the half head treated with the L'Oréal product.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A two step method for oxidatively coloring hair comprising a first step of applying to dark hair an alkalizing composition combined with an aqueous oxidizing agent for a period of time sufficient to lighten the hair up to or greater than two levels more than the base hair color shade, followed by a second step of applying an inactivated oxidative dye composition over the alkalizing composition combined with the aqueous oxidizing agent for a period of time sufficient to color the hair.

2. The method of claim 1 wherein the aqueous oxidizing agent composition additionally comprises one or more of a humectant, thickener, surfactant, conditioner, or preservative.

* * * * *